(12) United States Patent
Strauss et al.

(10) Patent No.: US 8,920,479 B2
(45) Date of Patent: Dec. 30, 2014

(54) ANTERIOR VERTEBRAL PLATE WITH SPIKE FIXATION

(75) Inventors: Kevin R. Strauss, Columbia, MD (US); Larry E. McClintock, Gore, VA (US); Todd M. Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 1437 days.

(21) Appl. No.: 11/694,403

(22) Filed: Mar. 30, 2007

(65) Prior Publication Data

US 2008/0255620 A1 Oct. 16, 2008

(51) Int. Cl.
*A61B 17/80* (2006.01)
*A61B 17/70* (2006.01)

(52) U.S. Cl.
CPC ............ *A61B 17/809* (2013.01); *A61B 17/7059* (2013.01)
USPC .......................................... 606/297; 606/286

(58) Field of Classification Search
USPC ......... 606/286, 297, 151, 280, 219, 281, 283, 606/284
See application file for complete search history.

(56) References Cited

U.S. PATENT DOCUMENTS

| 4,047,524 | A | * | 9/1977 | Hall | 606/75 |
|---|---|---|---|---|---|
| 4,434,796 | A | * | 3/1984 | Karapetian et al. | 606/75 |
| 4,456,006 | A | * | 6/1984 | Wevers et al. | 606/75 |
| 4,531,522 | A | * | 7/1985 | Bedi et al. | 606/220 |
| 4,651,724 | A | * | 3/1987 | Berentey et al. | 606/284 |
| 5,201,737 | A | * | 4/1993 | Leibinger et al. | 606/284 |
| 5,662,655 | A | * | 9/1997 | Laboureau et al. | 606/75 |
| 5,713,899 | A | * | 2/1998 | Marnay et al. | 623/17.11 |
| 5,718,705 | A | * | 2/1998 | Sammarco | 606/284 |
| 5,899,904 | A | * | 5/1999 | Errico et al. | 606/256 |
| 5,941,881 | A | * | 8/1999 | Barnes | 606/71 |
| 6,336,928 | B1 | * | 1/2002 | Guerin et al. | 606/282 |
| 6,620,165 | B2 | * | 9/2003 | Wellisz | 606/297 |
| 6,746,450 | B1 | * | 6/2004 | Wall et al. | 606/280 |
| 6,916,320 | B2 | * | 7/2005 | Michelson | 606/280 |
| 2003/0100898 | A1 | * | 5/2003 | Wellisz | 606/69 |
| 2004/0097935 | A1 | * | 5/2004 | Richelsoph et al. | 606/61 |
| 2004/0153078 | A1 | * | 8/2004 | Grinberg | 606/75 |
| 2006/0058796 | A1 | * | 3/2006 | Hartdegen et al. | 606/69 |
| 2006/0247681 | A1 | * | 11/2006 | De Canniere et al. | 606/219 |
| 2007/0123884 | A1 | * | 5/2007 | Abdou | 606/69 |
| 2008/0234750 | A1 | * | 9/2008 | Woods et al. | 606/291 |

* cited by examiner

*Primary Examiner* — Christian Sevilla

(74) *Attorney, Agent, or Firm* — Carter, DeLuca, Farrell & Schmidt, LLP

(57) ABSTRACT

Provided is a novel system that includes an anterior vertebral body plate with at least one bone spike pivotally attached to the plate and capable of being manually inserted into underlying bone to securely fix the plate to the bone. Also provided is a method of stabilizing cervical vertebrae using the disclosed system.

23 Claims, 7 Drawing Sheets

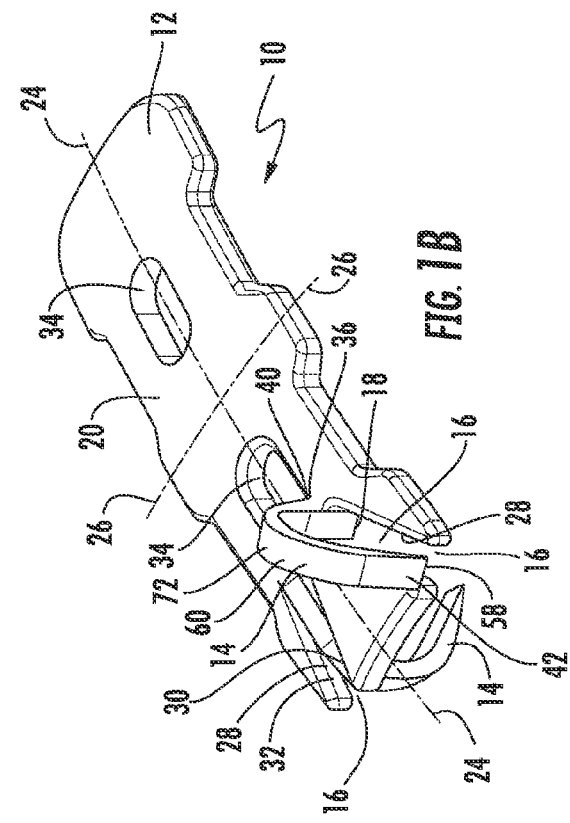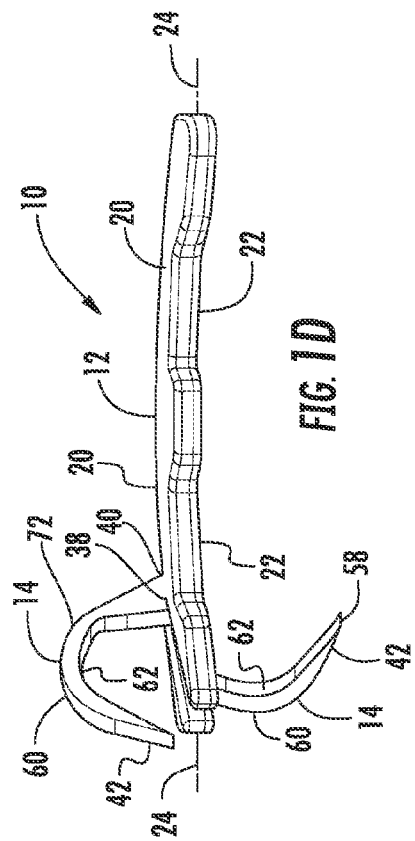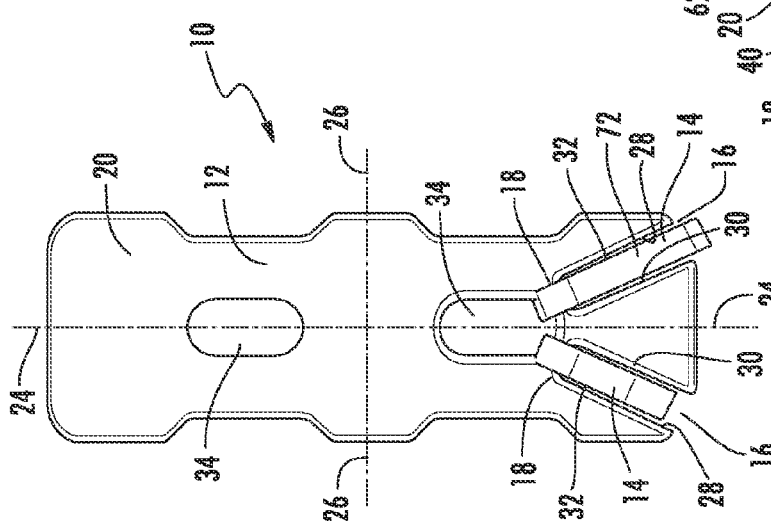

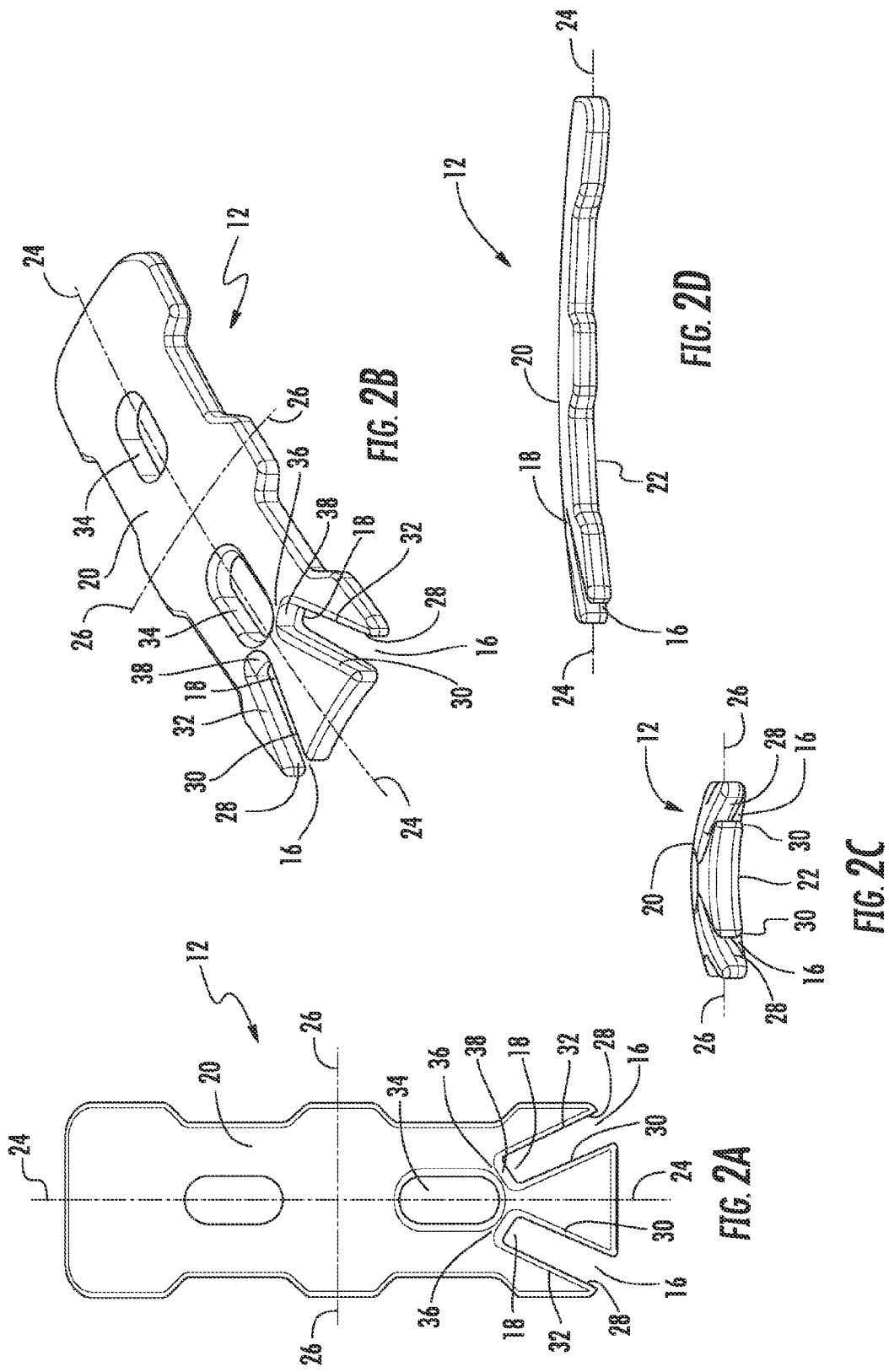

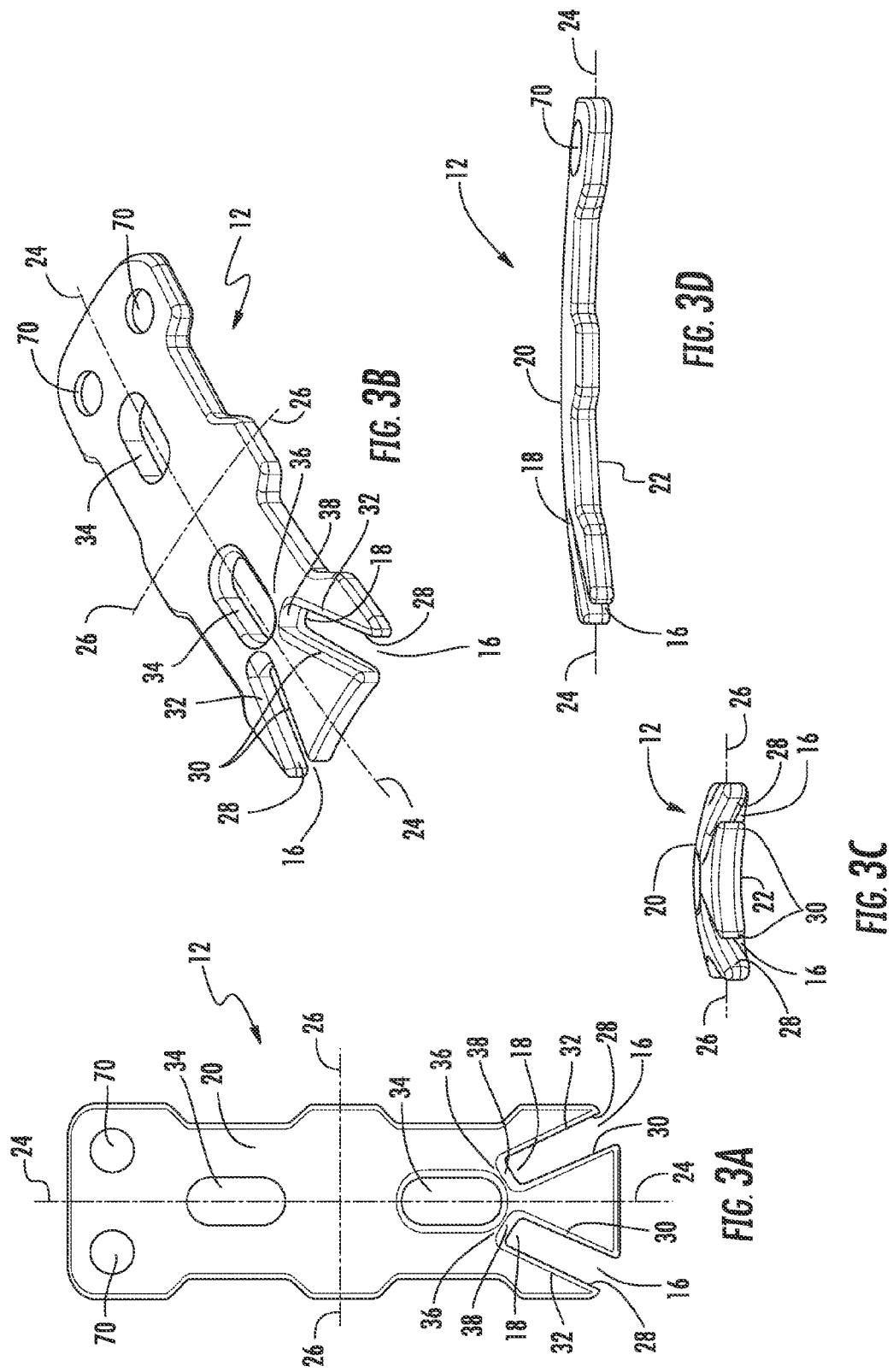

ANTERIOR VERTEBRAL PLATE WITH SPIKE FIXATION

BACKGROUND OF THE INVENTION

1. Technical Field

The present invention relates to devices and methods for use in orthopedic spine surgery. In particular, the present invention relates to a bone plate system that provides a low profile anterior vertebral body plate and at least one spike fixation element, the system being used for fixation and stabilization of the spine, the spike fixation elements being located proximate to at least one end of the plate to provide a secure attachment to the underlying bone.

2. Background Art

Disease, the effects of aging, or physical trauma resulting in damage to the spine has been treated in many instances by fixation or stabilization of the effected vertebra. The use of plates and screws for fixation and stabilization of the cervical vertebra has been widely accepted as a reliable practice and has proven to be highly successful clinically.

The various plates, which are attached to the anterior vertebral bodies of the spinal column by bone screws have some common features such as relatively planar body profiles that define multiple holes or slots through which the screws fit and are threaded into the bone. A common problem with plates affixed to bone using conventional bone screw attachments is the unintentional backing out of the screws from the underlying bone with a resulting loosening of the plate from the bone. Various means have been used to prevent the screws from becoming loose or detached from their necessary secured or locked attachment to the vertebral plate. Among the differences between the conventionally used plates and screws is the manner in which the screws are locked into place in the hole or slot of the plate after the screws have been secured to the bone.

These conventional devices attached to the underlying bone using only bones screws can be generally grouped into three basic categories with regard to how the screws are captured or secured in the plates.

Early plate designs were standard bone plates having holes through which screws were passed and screwed into the bone. These plates had no special provision for attaching the screws to the plate and as such were susceptible to having the screws back out of the plate over time. Later innovations included providing a screw head containing a threaded hole configured to receive a set screw, which was inserted into the screw head to expand the diameter of the screw head and frictionally engage the wall of the plate hole, thereby resisting forces which tend to cause the screw to back out. While such mechanisms have worked to some degree, the addition of a small additional part, the set screw, at the time of surgery presents the potential hazard of dropping the set screw into the surgical field or otherwise misapplying the set screw to the screw head, for example, cross threading.

Later alternative approaches included providing plates and/or screws with special features, which were specifically to hold the screw in position once the screw is inserted through the plate and screwed into the bone. One direction taken in this effort has been to design plates that incorporate or attach individual retaining rings, cams or snap features associated with each plate hole configured to hold the inserted screw in place relative to the plate.

Another approach is to add a cover to the plate after the screws have been placed. Such a design undesirably adds steps to the surgical procedure, thickness or height to the overall construct, and is susceptible to misapplication. Yet another direction taken in this effort to provide plates with locking elements is to provide dedicated overlying features, which are attached to the top side of the vertebral plate for the purpose of covering at least a portion of the screw head and thereby holding the screw in a seated and locked position. Generally these plates are designed to provide a variety of screw covering features that are pre-attached to the plate, and which can be selectively slid or rotated into position once it has been inserted. In some devices, such covering plates cover multiple screw heads. These plates typically require an increase in the overall composite thickness of the plate in order to accommodate the additional locking feature attached to the top side of the plate. This is a particularly unacceptable condition due to the use of such plates in an area of the spine where a thin, smooth surfaced profile for the plate assembly is preferred. Another major problem with such plates is that the overlying locking element cannot always be properly positioned over the screw head if the screw shaft was, due to anatomical necessity, positioned through the plate and into the bone at an angle such that the screw head does not fully seat in the plate recess provided on the top side of the plate. Further, when one of the overlying locking elements of such a plate loosens or becomes disengaged it is then free to float away from the top side of the plate and migrate into the soft tissue adjacent to the top side of the vertebral plate.

Yet another approach is to provide machine threads in the plate hole with corresponding threads on the screw head. Thus the screw has a first, bone engaging thread on its shaft and a second machine thread on the screw head. As the thread shaft is screwed into bone the screw head approaches the plate hole and the machine thread engages the thread in the hole. In practice there is nothing to prevent the same forces that urge the screw to back out of bone, allow the plate to loosen from the bone, and perhaps allow the loosened bone screw to interfere with and damage adjacent soft tissue.

These plates have been widely used; however, an inherent problem associated with such plates is the use of the additional very small retaining elements that can become disengaged from the plate and migrate into the surrounding soft tissues just as can the conventional unsecured bone screw. Further, difficulty experienced in accessing and disengaging the small locking elements and removing the screws from this type of plate has caused some concern for the continued use of such plates.

There is therefore, an unfulfilled need for an anterior cervical plate system that can maintain a relatively low profile while providing security from the bone screw backing out problems associated with conventional plate and bone screw systems. Further there is a need for a vertebral plate that does not have additional separate small locking elements as found in conventional devices with the predictable problems of those locking elements becoming disengaged from the plate and migrating away from the top side of the plate into the surrounding soft tissue.

SUMMARY OF THE DISCLOSURE

The present invention meets the above identified need by providing a low profile anterior vertebral body plate system, which is secured to the underlying bone using spike fixation elements.

Also provided is a low profile anterior vertebral body plate system, which is secured to the underlying bone using at least one spike fixation element that is configured to be inserted into and affixed to the underlying bone by a single manual insertion action.

Also provided is a low profile anterior vertebral body plate system, which is secured to the underlying bone using at least one spike fixation element that is preassembled to the body plate.

Also provided is a low profile anterior vertebral body plate system, which is secured to the underlying bone using multiple spike fixation elements that are configured to be inserted into and affixed to the underlying bone by a single manual insertion action.

Also provided is a low profile anterior vertebral body plate system, which is secured to the underlying bone using multiple spike fixation elements, at least two of the spike fixation elements being moveably connected to opposing ends of the plate.

Also provided is a low profile anterior vertebral body plate system, which is secured to the underlying bone using two pair of spike fixation elements, each pair of the spike fixation elements being moveably connected to opposing ends of the plate.

Also provided is a low profile anterior vertebral body plate system, which is secured to the underlying bone using at least one spike fixation element and at least one bone screw.

Also provided is a method of manufacture of a low profile anterior vertebral body plate system.

Also provided is method of applying a low profile plate system to the surface of a bone.

Also provided is a method of stabilizing spinal vertebrae, the method including providing a low profile anterior vertebral body plate system, the plate being securely attached to the underlying bone of adjacent vertebrae using at least one spike fixation element so as to hold one attached vertebra in a fixed position relative to the adjacent attached vertebra.

Also provided is a kit, which includes at least one low profile anterior vertebral body plate configured for attachment of spike fixation elements, a corresponding set of spike fixation elements and at least one other spinal device, tool, or instrument.

BRIEF DESCRIPTION OF THE DRAWINGS

The foregoing and other features of the novel low profile anterior vertebral plate system will become apparent to one skilled in the art to which the disclosed system and devices relate upon consideration of the following description of exemplary embodiments with reference to the accompanying drawings, wherein:

FIGS. 1A-F respectively show top, top isometric, end, side, bottom, and bottom isometric views of the low profile anterior vertebral plate system including a vertebral plate and multiple spike fixation elements, one of the spike fixation elements being in an open or ready position relative to the plate and the other spike fixation element being in the closed or fully inserted position relative to the plate.

FIGS. 2A-D respectively show top, isometric, end, and side views of the vertebral plate included in the system shown in FIGS. 1A-F.

FIGS. 3A-D respectively show top, isometric, end, and side views of an alternative vertebral plate that can be used with the anterior vertebral plate system, the alternative plate including at least one bone screw hole.

FIG. 5B shows one of the spike fixations elements being configured with an alternative pointed insertion end.

DETAILED DESCRIPTION OF PREFERRED EMBODIMENTS

Figures 1E, 1F:
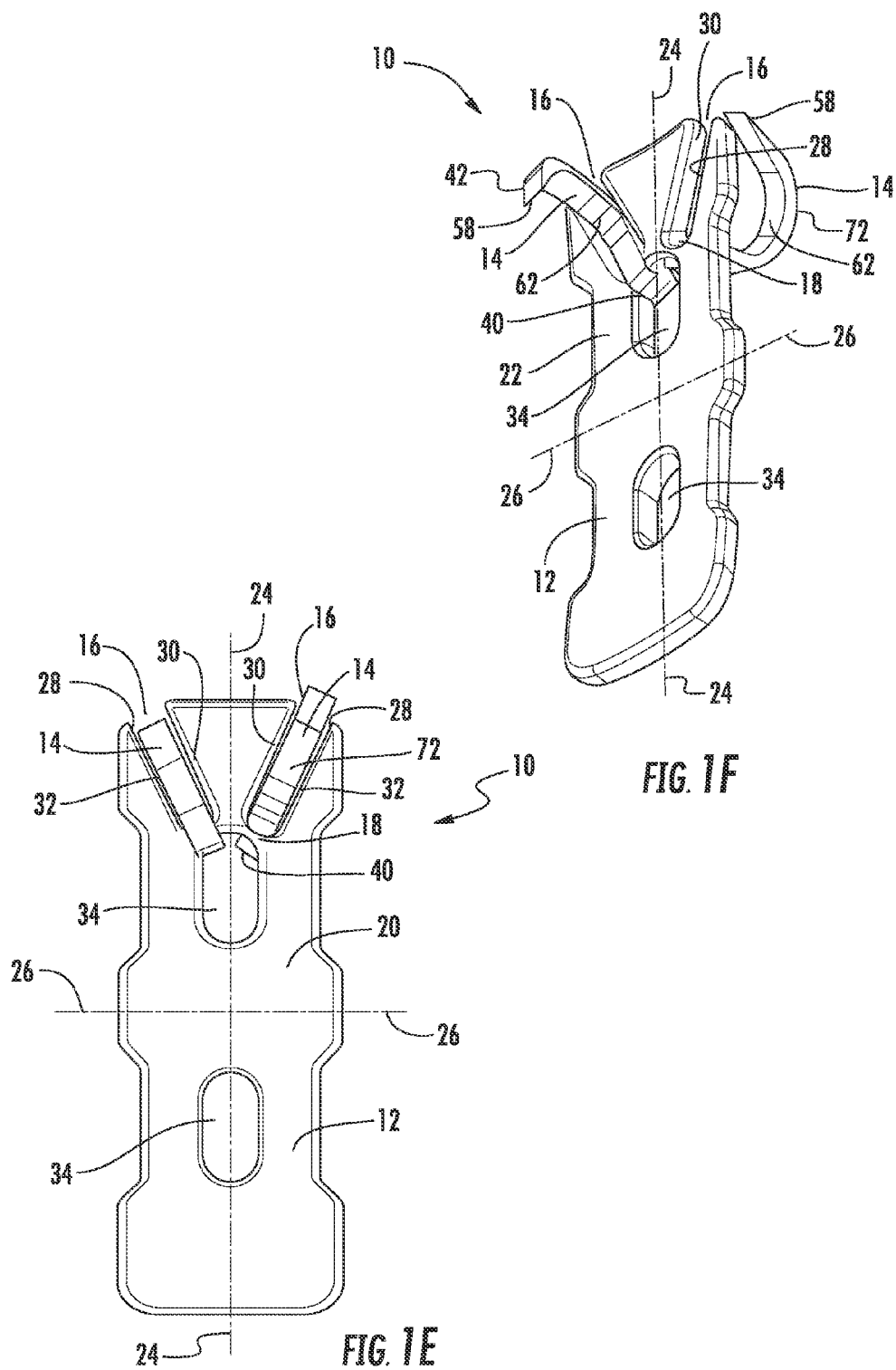

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

The system, as generally shown at 10 in FIGS. 1A-F, 5A-B, and 6A-B includes a low profile anterior vertebral body plate 12 that, when implanted in a patient, can be secured to the underlying bone using at least one bone spike 14. The vertebral body plate 12, as shown in FIGS. 1A-F, 2A-D, 3A-D, 5A-B, and 6A-B can be provided as an elongated, low profile, plate structure that defines at least one and preferably multiple spike slots 16, which are sized and configured to enable pivotal connection to a corresponding bone spike 14. The bone spike 14, as separately shown in FIGS. 4A-D and shown assembled to the bone plate 12 in FIGS. 1A-F, 5A-B, and 6A-B is configured to be pivotally connect to a spike connection end 18 of slot 16.

As shown in FIGS. 1A-F, 2A-D, 3A-D, 5A-B, and 6A-B the plate 12 can be configured to be generally planar; however, the plate preferably will be formed to have arcuate upper and lower surfaces 20, 22, arcing along both the longitudinal axis 24 as well as the transverse axis 26 of the plate 12. This arcing of the plate surface provides a better conformational fit to the anterior surface of the vertebrae to which the plate is to be attached. As shown in FIGS. 2A-B and 3A-B, the spike slots 16 are defined in the body of the plate 12 to be open-ended slots. These open-ended spike slots 16 have two slot side walls 28, 30 extending inwardly from the outer edge of the plate 12 to the spike connection end 18 to form a three-sided open-ended slot. The side walls 28, 30 of the spike slot 16 are preferably parallel one to the other, although a spike slot 16 having non-parallel side walls 28, 30 would still be within the inventor's concept of the system 10. The side walls 28, 30 of the spike slot 16 are of sufficient distance one from the other so as to permit the bone spike 14 to traverse through the spike slot 16 as it pivots about the spike connection end 18 of the spike slot 16. At least one plate portal 34 is defined extending through the body of the plate 12 from the upper 20 to the lower 22 surface of the plate. As best shown in FIGS. 2A-B and 3A-B, the spike slot 16 extends inwardly toward the plate portal 34 and terminates at the spike connection end 18, which is proximate to the plate portal 34. As shown in FIGS. 1A-F, 5A-B, and 6A-B the portion of the plate 12 between the spike connection end 18 and the adjacent portion of the side wall of the plate portal 34 is of a size and configuration appropriate to facilitate the pivotal connection of the bone spike 14 to the plate 12. The spike pivot portion 36 of the plate 12 is provided at the spike connection end 18 with a plate pivot surface 38, which can have a generally convex form to facilitate the rotational movement of the bone spike 14 in its pivotal connection to the plate 12.

Figure 4A:
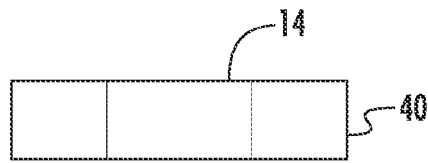
FIGS. 4A-C respectively show top, isometric, and side views of the spike fixation element included in the system shown in FIGS. 1A-F.
Figure 4B:
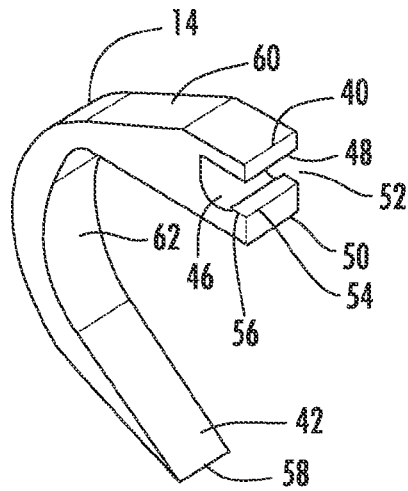
Figure 4C:
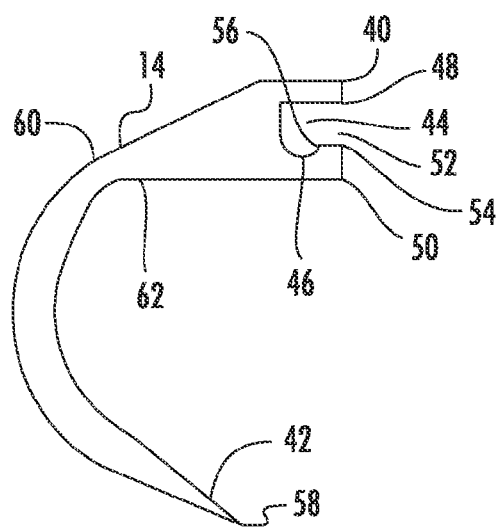
Figure 4D:
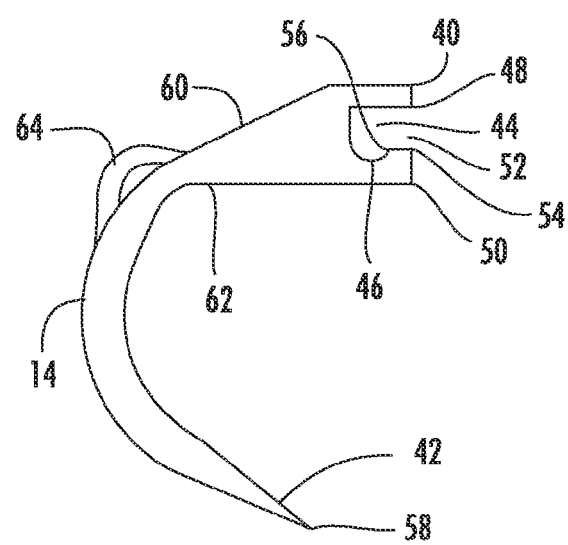
FIG. 4D shows a side view of a spike fixation element for use with the vertebral plate spike fixation system, the spike fixation element being provided with a spike grasping fixture.

The bone spike 14, as shown in FIGS. 1A-F, 4A-D, 5A-B, and 6A-B can be provided as a generally arcuate or hook-like elongated element having a first end 40 and a second end 42. The first end 40 of the bone spike 14 defines an inwardly directed plate connection recess 44 that is sized configured to accept the spike pivot portion 36 of the plate 12 within the connection recess 44. As best shown in FIGS. 4B, 4C, and 4D, at least a portion of the connection recess 44 is configured to have a spike pivot surface 46 having a concave shape that is complementary to the convex shaped plate pivot surface 38 of the plate 12. The upper terminal edge 48 and the lower terminal edge 50 of the plate connection recess 44 are spaced apart one from the other to define a recess opening 52, which is sized to permit passage of the spike pivot portion 36 of the plate 12 into the recess connection 44 of the bone spike 14. In addition, the lower terminal edge 50 supports a spike securing element 54, the inner most portion of which is the outermost edge 56 of the spike pivot surface 46. When the bone spike 14 is pivotally moved into a fully inserted position, the spike securing element will have rotated partially around the spike pivot portion 36 of the plate 12 so as to snap fit the spike securing element 54 into a secured position within the plate portal 34.

Figure 5A:
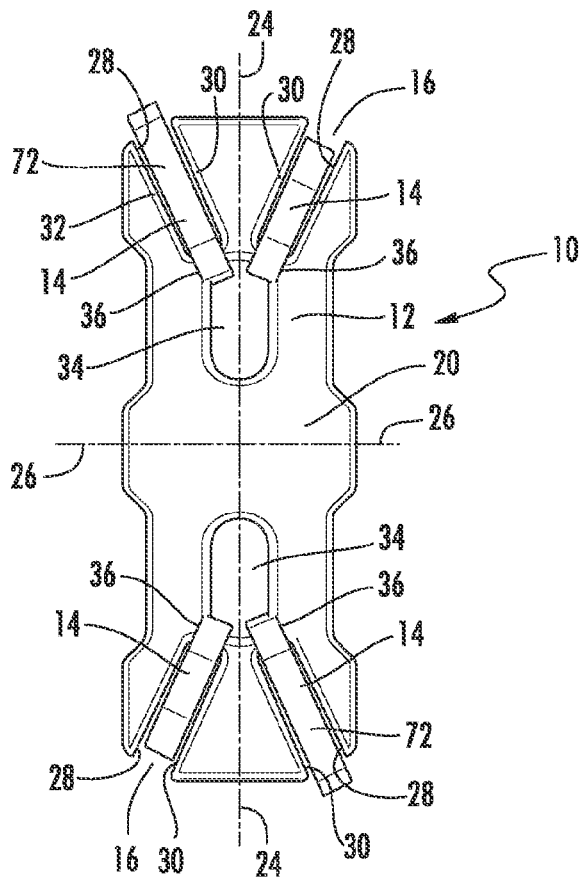
FIGS. 5A-B respectively show top and isometric views of the low profile anterior vertebral plate system including a vertebral plate and two pair of opposing spike fixation elements, one member of each pair of the spike fixation elements being in an open or ready position relative to the plate and the other member of each pair of the spike fixation elements being in the closed or fully inserted position relative to the plate.
Figure 5B:
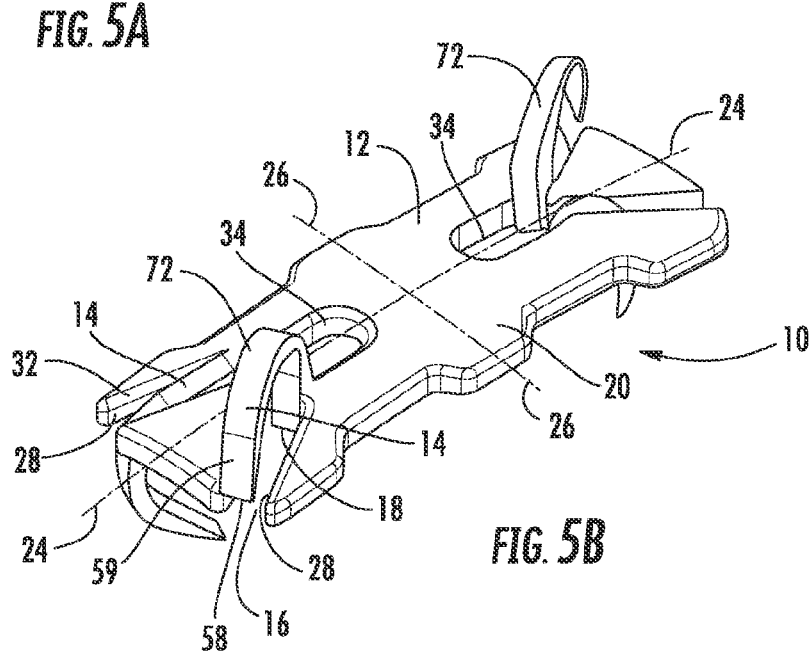
Figure 6A:
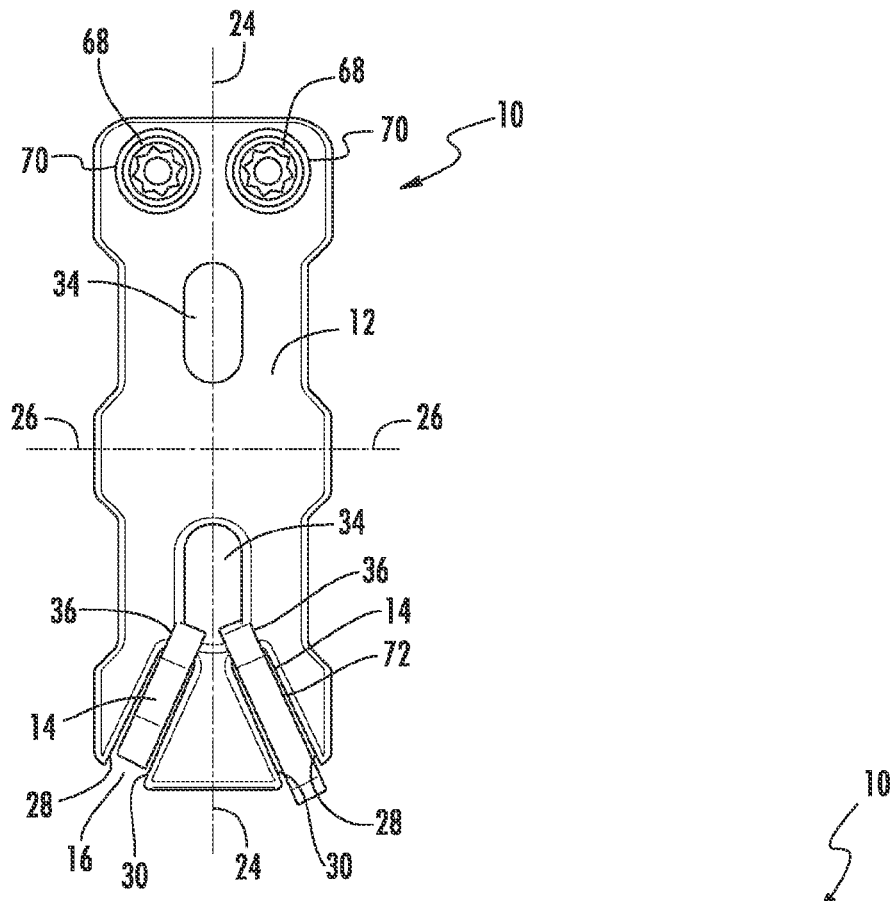
FIGS. 6A-B respectively show top and isometric views of the low profile anterior vertebral plate system including a vertebral plate having a pair of spike fixation elements at one end of the plate and a pair of bone screw holes with fully inserted bone screws at the opposing end of the plate, one member of the pair of spike fixation elements being in an open or ready position relative to the plate and the other member of the pair of the spike fixation elements being in the closed or fully inserted position relative to the plate.
Figure 6B:
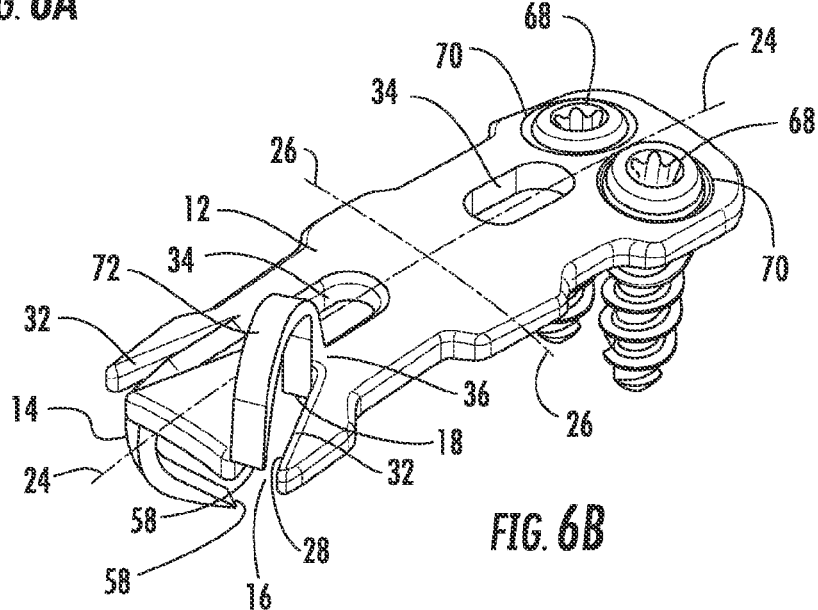

As shown in, shown in FIGS. 1B, 1C, 1D, and 1F, as well as FIGS. 4B-D, 5B and 6B, the second end 42 of the bone spike 14 can terminate in a sharpened bone penetrating end 58. The sharpened bone penetrating end 58 can be provided with a sharpened knife-like configuration suitable for penetrating cortical bone as the bone spike 14 is rotated downward from the plate 12. As shown in FIG. 5B, a spike retention element 59 can be provided on the upper or lower surface 60, 62 near the penetrating end 58 of the spike 14. The spike retention element 59 can be configured as a barb, similar to that used on a fish hook, although any configuration for the retention element 59 can be employed that serves to retard the unintentional withdrawal of the fully inserted spike 12 from the bone. Also shown in FIG. 5B is an alternative pointed configuration for the sharpened bone penetrating end 58. Other configurations of the bone penetrating end 58 can also be employed provided the end 58 is capable of penetrating cortical bone upon the application of manual downward force on the pivotally connected bone spike 14.

The bone spike 14 has a spike upper surface 60 and a spike lower surface 62, which due to the generally downward arcuate form of the bone spike 14 will be respectively of a convex shape and concave shape. The degree of downward curvature of the generally arcuate shaped bone spike 14 is such that when fully inserted into the bone, the bone penetrating end 58 of the bone spike 14 will be positioned within the underlying bone and beneath the body of the plate 12. When so positioned, the bone spike 14 provides a secure attachment to the underlying bone and thus provides stability to the bone plate system 10 in its attachment to the bone. As shown in FIG. 4D, the spike upper surface 60 can be provided with a tool contact element 64 that is configured to facilitate tool attachment to the spike for the purpose of insertion and/or retraction of the bone spike 14 through cortical bone. A non-limiting example of a tool contact element 64, as shown in FIG. 4D, has an eyelet-like configuration; however, the tool contact element 64 can be of any shape or size that is capable of facilitating connection of a tool to the bone spike 14. Non-limiting examples of configurations of the tool contact element 64 include an inwardly directed or outwardly directed eyelet, a hook, a textured protrusion, a textured recess, and combinations thereof.

As best shown in FIGS. 2A-D and 3A-D, the spike slot 16 can be defined in the body of the plate 12 at an acute angle to the longitudinal axis 24 of the plate 12. This angled position of the spike slot 16, which necessarily control the direction of entry of the pivotally attached bone spike 14, provides additional stability of the plate 12 in both the longitudinal and transverse planes relative to the underlying bone to which the system 10 is attached. The system 10 includes at least one bone spike 14; however, it is preferred that multiple bone spikes be employed to connect the bone plate 12 to underlying bone. As shown in FIGS. 5A-B, the system 10 can be configured to have at least four spike slots 16 with at least 4 corresponding pivotally connected bone spikes 14.

As shown in FIGS. 3A-D, and 6A-B, the system 10 can also be provided with both bone spike 14 connections and bone screw 68 connections to secure the bone plate 12 to the underlying bone. As shown in FIGS. 3A-D, the bone screw holes 70, which are defined as through passages in the plate 12, can be sized and configured to securely receive a respective bone screw 68. The bone screws 68 and bone screw holes 70 can be of any known design, including that of a bone screw capable of being locked into position in the bone plate 12.

In practice, the plate 12 can be preassembled with the bone spikes 14 to provide a system 10 that is ready for insertion into a patient and for connection to the anterior surface of the vertebral body without the need for additional locking elements. In an unlocked and ready configuration, the system 12 presents each of the pivotally connected bone spikes 14 in a raised position 72 as shown in FIGS. 1A-F, 5A-B, and 6A-B. After properly positioning the plate 12 on the surface of the bone, the bone spikes 14 can be manually pushed into and through the cortical bone underlying the bone plate 12, the bone penetrating end 58 of the bone spikes 14 acting to breach the cortical bone and ease the process of insertion of the bone spikes 14. If necessary, the tool contact element 64 on the upper surface 60 of the bone spike 14 can be contacted by an insertion tool to facilitate the insertion process. The bone spike 14 can be pushed inward into the bone until the pivotal rotation of the bone plate 14 reaches a position relative to the spike pivot portion 36 of the plate 12 where the spike securing element 54 reaches the edge of the plate portal 34 and makes the snap fit connection between the securing element 54 and the plate portal 34, thus providing a locking connection for the bone spike 14. If a system 10 is employed that includes both bone spike 14 connections and bone screw 68 connections, as demonstrated in FIGS. 5A-B, bone screws 68 can be inserted through the bone plate 12 and into the underlying bone either before or after the bone spikes 14 have been inserted into the underlying bone.

If it is subsequently determined necessary to remove the system 10 from the underlying bone to which it was earlier attached, the bone spikes 14 can be manually pivotally rotated upward with sufficient force to disengage the locking connection of the spike securing element 54 from the edge of the plate portal 34. The bone spike 14 can then be easily pivotally rotated out of the underlying bone. This retraction of the bone spikes 14 can be accomplished, if necessary, by employing a retraction tool suited to connect to the tool contact element 64 on the upper surface 60 of the bone spike 14. For a system 10 employing both bone spikes 14 and bone screws 68, the removal of the bone screws 68 can be accomplished in a manner and using tools appropriate for the type of bone screw 68 employed.

Advantageously, the system 10, using only bone spikes 14 for connection to the underlying bone requires no additional small locking elements as are used in many conventional efforts to provide a locking method for vertebral plate devices.

The above described method of use of the system 10 can be employed as a method of stabilizing or fixing injured or diseased vertebrae and if necessary, multiple devices or a device, which is elongated beyond the examples depicted herein, can be employed as necessary so as to secure more than two vertebrae together.

While the device as described herein can be preferably used to attach to the anterior surface of cervical vertebrae and is configured to be capable of stabilizing cervical vertebrae, it is within the inventors' understanding that the plate can be configured and adapted to conform to any implantable surgical plate requirement to provide a low profile plate capable of securing and stabilizing any injured or diseased bone.

The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose. It is conceivable that some components of the device can be made from plastics, composite materials, and the like. It is also conceivable that the bone plate 12 and the bone spikes 14 can be integrally formed, the connection point of the spikes 14 to the plate 12 being manufactured of a material that can with sufficient force be bent to permit a rotation of the bone spike 14 downward and into underlying bone beneath the plate 12.

It is also within the concept of the inventors to provide a kit, which includes at least one of the bone plate systems 10 disclosed herein. The kit can also include additional orthopedic devices and instruments; such as for example, instruments for implanting the system and fixing the bone spikes 14 into bone, removing the bone spikes from the bone, bone screws, instruments for tightening or loosening bone screws, spinal rods, hooks or links and any additional instruments or tools associated therewith. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A bone plate system, comprising:
    a plate having an upper surface and a lower surface, said plate defining at least one bone spike slot, at least one bone spike sized and configured to selectively attach to said plate and configured to pivotally connect to and pivotally move radially inward within said bone spike slot from a raised position above said upper surface of said plate for positioning said plate over underlying bone to an inserted position beneath said upper surface of said plate for securing said plate to said underlying bone.

2. The bone plate system of claim 1, comprising at least two bone spike slots and two bone spikes.

3. The bone plate system of claim 1, comprising four bone spike slots and four bone spikes.

4. The bone plate system of claim 1, wherein said plate is an anterior vertebral body plate.

5. The bone plate system of claim 1, further including at least one bone screw and wherein said plate comprises at least one bone screw hole.

6. The bone plate system of claim 1, wherein said plate is configured to have an upper and a lower curved surface, said upper and lower curved surfaces being curved along a longitudinal axis of said plate.

7. The bone plate system of claim 1, wherein said plate is configured to have an upper and a lower curved surface, said upper and lower curved surfaces being curved along a transverse axis of said plate.

8. The bone plate system of claim 6, wherein said upper and lower curved surfaces are curved also along a transverse axis of said plate.

9. The bone plate system of claim 1, wherein said bone spike slot is not aligned with said longitudinal axis of said plate.

10. The bone plate system of claim 1, wherein said bone spike slot is aligned at an acute angle relative to said longitudinal axis of said plate.

11. The bone plate system of claim 1, wherein said bone spike can be rotated downward into a fully inserted and locked position.

12. The bone plate system of claim 11, wherein said locked position is capable of being released to permit withdrawal of said spike.

13. The bone plate system of claim 1, said bone spike comprising a spike retention element that is sized and configured to be capable of resisting unintentional withdrawal of said spike from a fully inserted position.

14. The bone plate system of claim 1, wherein said bone spike has an upper surface, said upper surface having a tool contact element.

15. The bone plate system of claim 14, wherein said tool contact element has a configuration selected from the group consisting of an eyelet, a hook, a textured protrusion, a textured recess, and combinations thereof.

16. The bone plate system of claim 14, wherein said tool contact element is configured to receive a tool capable of facilitating rotational movement of said bone spike relative to said bone plate.

17. A method of stabilizing a vertebral body, the method comprising,
    surgically accessing an anterior surface of a vertebral body in need of stabilization;
    positioning a bone plate over said vertebral body, said bone plate having an upper surface and a lower surface and defining at least one bone spike slot, said bone plate including at least one bone spike sized and configured to selectively attach to said bone plate and configured to pivotally connect to and pivotally move radially inward within said bone spike slot;
    moving said at least one bone spike from a raised position above said upper surface of said plate to an inserted position beneath said upper surface of said bone plate for securing said plate to said vertebral body.

18. A method of stabilizing a vertebral body according to claim 17, wherein said bone plate further comprises at least one bone screw hole and one bone screw.

19. A kit comprising:
at least one low profile anterior vertebral body plate configured for attachment of spike fixation elements; and
a set of bone spikes, each bone spike of said set of bone spikes sized and configured to selectively attach said vertebral body plate and configured to pivotally connect to and pivotally move within each of a corresponding set of bone spike slots operably associated with said vertebral body plate, each bone spike of said set of bone spikes movable within each of said set of bone spike slots from a raised position above an upper surface of said vertebral body plate for positioning said vertebral body plate over underlying bone to an inserted position beneath said upper surface of said vertebral body plate for securing said vertebral body plate to underlying bone,
wherein each bone spike of said set of bone spikes includes a connection end for releasably connecting to a pivot portion of each of said set of bone spike slots, wherein pivotable movement of each bone spike of said set of bone spikes within each of said corresponding set of bone spike slots from said raised position to said inserted position moves said connection end into a locking position to facilitate securing said vertebral body plate to underlying bone.

20. The kit according to claim 19, further comprising at least one other spinal device, tool or instrument.

21. The bone plate system of claim 1, wherein said bone spike is configured to pivotally connect to and pivotally traverse through said bone spike slot from said raised position above said upper surface of said plate for positioning said plate over underlying bone to said inserted position beneath said upper surface of said plate for securing said plate to said underlying bone.

22. The bone plate system of claim 1, wherein rotation of said bone spike to said inserted position defines a locking connection between said plate and said bone spike.

23. The kit according to claim 19, wherein said bone spike is pivotally coupled to said vertebral body plate.

* * * * *